(12) United States Patent
Chan et al.

(10) Patent No.: US 6,290,705 B1
(45) Date of Patent: Sep. 18, 2001

(54) IRRIGATING FORCEPS

(75) Inventors: Kwan Y. Chan, Fort Worth; David A. Eister, Mansfield, both of TX (US)

(73) Assignee: Alcon Universal Ltd. (CH)

( * ) Notice: Subject to any disclaimer, the term of this patent is extended or adjusted under 35 U.S.C. 154(b) by 0 days.

(21) Appl. No.: 09/467,411

(22) Filed: Dec. 20, 1999

(51) Int. Cl.$^7$ ........................................ A61F 9/00
(52) U.S. Cl. .................. 606/107; 606/205; 606/207; 606/210
(58) Field of Search ..................... 606/107, 205, 606/206, 210, 211, 160, 161, 166; 30/186, 191, 115, 116, 117, 304

(56) References Cited

U.S. PATENT DOCUMENTS

| | | | |
|---|---|---|---|
| 3,916,909 | 11/1975 | Kletschka et al. | 128/354 |
| 3,980,086 | 9/1976 | Kletschka et al. | 128/318 |
| 4,225,667 | 9/1980 | Ruben | 433/162 |
| 5,167,618 | 12/1992 | Kershner | 604/22 |
| 5,217,464 | * 6/1993 | McDonald | 606/107 |
| 5,630,821 | * 5/1997 | Klaas | 606/107 |
| 5,752,960 | * 5/1998 | Nallakrishnan | 606/107 |
| 5,860,985 | * 1/1999 | Anschultz | 606/107 |

* cited by examiner

Primary Examiner—Pedro Philogene
(74) Attorney, Agent, or Firm—W. David Lee

(57) ABSTRACT

A microsurgical forceps having a first handle and a second handle coupled to the first handle at a hinge point is disclosed. The first handle includes a cannula for transporting surgical fluid and a first jaw with an aperture for delivering the fluid. The second handle includes a second jaw for cooperating with the first jaw. The first handle may include a second cannula for fluidly coupling to a vacuum source. The first jaw may also include a second aperture for delivering vacuum. The forceps may be used to more effectively position an intracorneal optical lens in an intracorneal pocket.

12 Claims, 4 Drawing Sheets

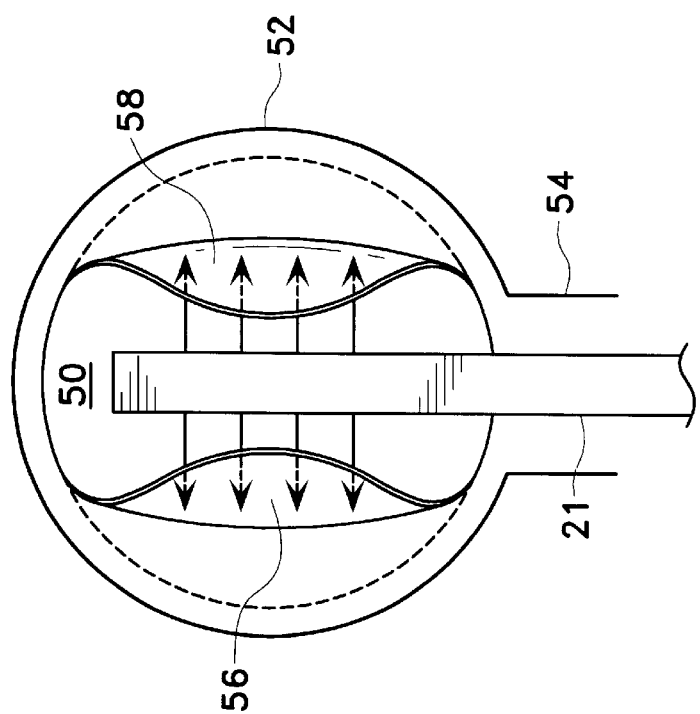
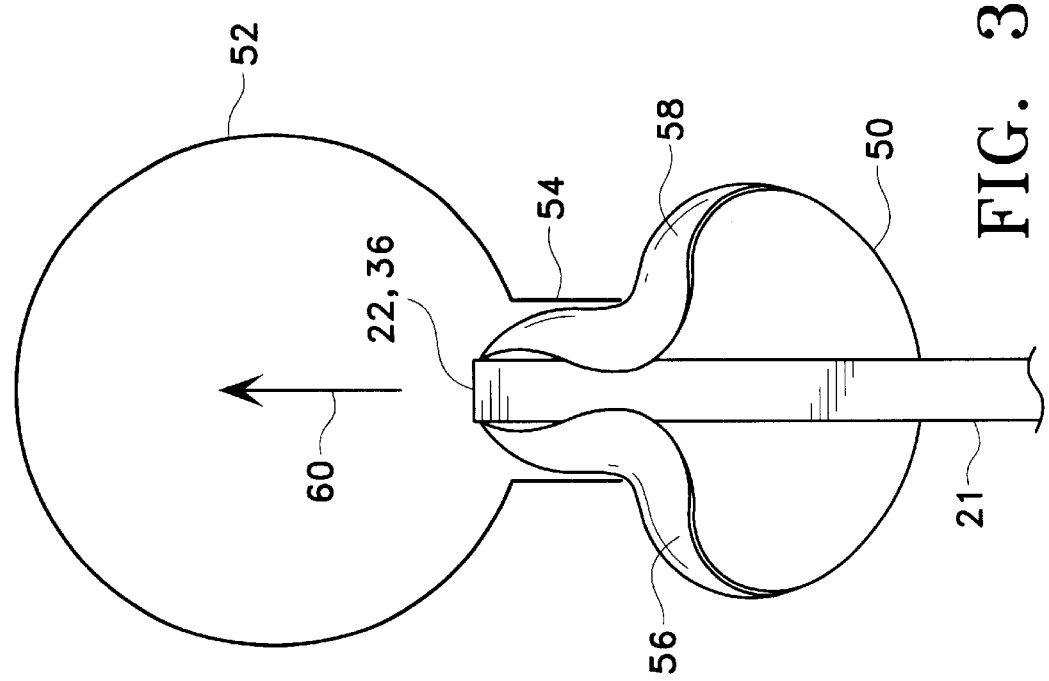
FIG. 3
FIG. 4

IRRIGATING FORCEPS

FIELD OF THE INVENTION

The present invention relates generally to microsurgical instruments and more specifically, but not by way of limitation, to microsurgical instruments suitable for the implantation of intracorneal optical lenses (ICOLs).

DESCRIPTION OF THE RELATED ART

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has been used is radial and/or transverse incisional keratotomy (RK or AK, respectively). Photoablative lasers have also been used to reshape the surface of the cornea (photorefractive keratectomy or PRK) or for mid-stromal photoablation (Laser-Assisted In Situ Keratomileusis or LASIK). All of these refractive surgical procedures cause an irreversible modification to the shape of the cornea in order to effect refractive changes, and if the correct refraction is not achieved by the first procedure, a second procedure or enhancement must be performed. Additionally, the long-term stability of the correction is variable because of the variability of the biological wound healing response between patients.

Permanent intracorneal implants made from synthetic materials are also known for the correction of corneal refractive errors. Such implants may be generally classified into two categories.

One category is intracorneal implants that have little or no refractive power themselves, but change the refractive power of the cornea by modifying the shape of the anterior surface of the cornea. U.S. Pat. No. 5,123,921 (Werblin, et al.); U.S. Pat. Nos. 5,505,722, 5,466,260, 5,405,384, 5,323, 788, 5,318,047, 5,312,424, 5,300,118, 5,188,125, 4,766,895, 4,671,276 and 4,452,235 owned by Keravision and directed to intrastromal ring devices; and U.S. Pat. No. 5,090,955 (Simon), U.S. Pat. No. 5,372,580 (Simon, et al.), and WIPO Publication No. WO 96/06584 directed to Gel Injection Adjustable Keratoplasty (GIAK) all disclose examples of this category of implant.

A second category is intracorneal implants having their own refractive power. U.S. Pat. No. 4,607,617 (Choyce); U.S. Pat. No. 4,624,669 (Grendahl); U.S. Pat. No. 5,628,794 (Lindstrom); and U.S. Pat. Nos. 5,196,026 and 5,336,261 (Barrett, et al.) provide several examples of this category. In addition, U.S. patent application Ser. No. 08/908,230 filed Aug. 7, 1997 entitled "Intracorneal Diffractive Lens", which is incorporated herein in its entirety by reference, discloses an example of an ICOL that has both refractive and diffractive powers.

Microsurgical instruments used for the implantation of such intracorneal implants have also been developed. For example, WIPO Publication No. WO 99/30645 owned by Keravision discloses a variety of instruments for creating grooves in the stromal tissue for implanting a ring-shaped intacorneal implant or a pocket for implanting ICOLs. These tools may be used manually, but are preferably used in cooperation with a vacuum centering device. Another instrument used for creating an intracorneal pocket for implanting an ICOL is described in U.S. patent application Ser. No. 09/434,912 filed Nov. 5, 1999 entitled "Lamellar Dissecting Instrument", which is incorporated herein in its entirety by reference. However, after formation of an intracorneal pocket, an ICOL is typically positioned within the intracorneal pocket using conventional forceps, such as intraocular lens folding forceps. With conventional forceps, a surgeon must spend several minutes "spreading out" or flattening the ICOL within the intracorneal pocket and manipulating it into proper position within the pocket.

Accordingly, need exists for a microsurgical instrument that more effectively positions an ICOL within an intracorneal pocket. The instrument should be easy for the surgeon to use, should maximize patient safety, and should be economically feasible.

SUMMARY OF THE INVENTION

One aspect of the present invention is a microsurgical forceps for positioning an intracorneal optical lens within an intracorneal pocket. The forceps includes a first handle having a cannula for transporting surgical fluid and a first jaw with an aperture for delivering the fluid. The cannula is for fluidly coupling to a reservoir of the fluid, and the first jaw is for receiving the lens in a folded position around the first jaw. The aperture ejects the fluid in an outward direction from the first jaw to help unfold the lens. The forceps also includes a second handle coupled to the first handle at a hinge point. The second handle has a second jaw for cooperating with the first jaw.

BRIEF DESCRIPTION OF THE DRAWINGS

For a more complete understanding of the present invention, and for further objects and advantages thereof, reference is made to the following description taken in conjunction with the accompanying drawings in which:

FIG. 3 is an enlarged, top, fragmentary view schematically illustrating the insertion of an ICOL into an intracorneal pocket using the forceps of FIG. 1;

FIG. 4 is an enlarged, top, fragmentary view schematically illustrating the positioning of an ICOL within an intracorneal pocket using the forceps of FIG. 1.

DETAILED DESCRIPTION OF THE PREFERRED EMBODIMENTS

The preferred embodiments of the present invention and their advantages are best understood by referring to FIGS. 1 through 5 of the drawings, like numerals being used for like and corresponding parts of the various drawings.

Figure 1:
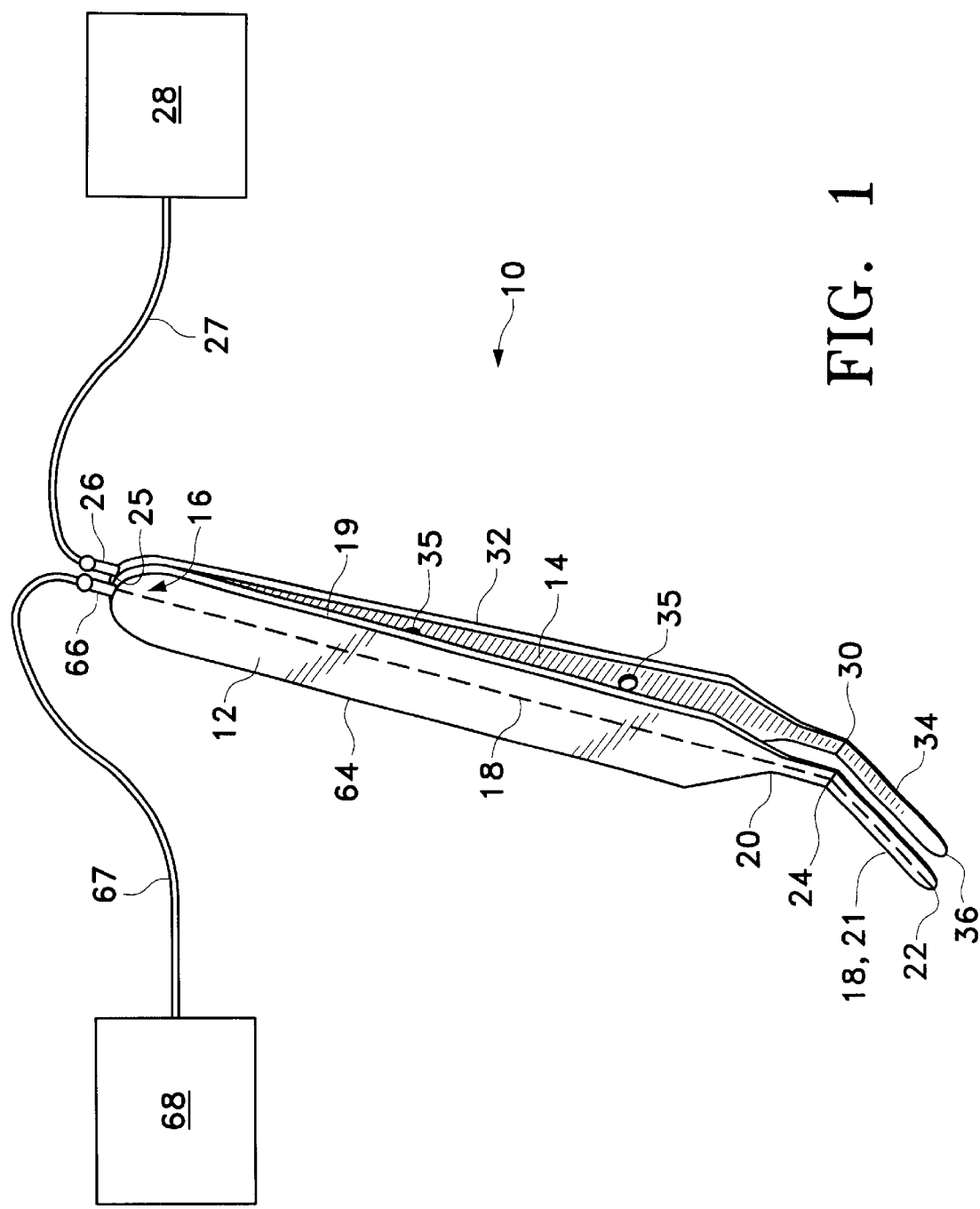
FIG. 1 is a perspective view schematically illustrating forceps according to a preferred embodiment of the present invention.

FIG. 1 illustrates microsurgical forceps 10 according to a preferred embodiment of the present invention. Forceps 10 are preferably used in the implantation of an intracorneal optical lens (ICOL) within an intracorneal pocket. However, forceps 10 may be used for positioning other lenses, devices, or implants within the eye or within other non-ocular body tissue. For convenience of description, but not by way of limitation, the present invention will be described hereinbelow with reference to implanting an ICOL within an intracorneal pocket.

Forceps 10 include an upper handle 12 and a lower handle 14 coupled at a hinge point 16. A cannula 18 is disposed within upper handle 12. Alternatively, although not shown in FIG. 1, cannula 18 may be coupled along a side of handle 12, such as side 19. Cannula 18 extends from the distal portion of upper handle 12 at a point 20. This portion of cannula 18 forms an upper jaw 21 of forceps 10. Cannula 18 preferably has a rounded end 22 and a bend 24. The portion of cannula 18 disposed within upper handle 12 and the portion of cannula 18 extending beyond bend 24 are preferably disposed at an angle of about 120 degrees to about 150 degrees relative to one another to facilitate the use of forceps 10 by a surgeon. Cannula 18 also extends from a proximal end 25 of forceps 10 and terminates in a port 26. Port 26 is for fluidly coupling with a reservoir 28. Such coupling is preferably performed using medical grade silastic tubing 27. Reservoir 28 may comprise a syringe, a pumping device, or other conventional apparatus for providing pressurized surgical fluid. Surgical fluid 18 may be saline solution, BSS PLUS® intraocular irrigating solution available from Alcon Laboratories, Inc. of Fort Worth, Tex., or another irrigating solution.

Lower handle 14 is formed with a bend 30 so as to mate with a bottom surface of upper handle 12. Lower handle 14 has a proximal portion 32 above bend 30 and a lower jaw 34 extending beyond bend 30. Lower jaw 34 preferably has a rounded end 36. Proximal portion 32 and lower jaw 34 are preferably disposed at an angle of about 120 degrees to about 150 degrees relative to one another.

When a user squeezes upper handle 12 and lower handle 14 together, upper jaw 21 and lower jaw 34 move toward one another. When a user quits exerting such pressure on upper handle 12 and lower handle 14, upper jaw 21 and lower jaw 34 move away from one another to a natural, unbiased spacing determined by the geometry and material properties of forceps 10. When a user squeezes upper handle 12 and lower handle 14 completely together, upper jaw 21 and lower jaw 34 are preferably spaced about 0.1 mm apart. This spacing corresponds to the typical thickness of an ICOL. Stops 35 may be disposed on the internal surface of proximal portion 32 of lower handle 14 or the internal surface of upper handle 12 to facilitate this spacing.

Upper jaw 21 preferably has a length of about 12 mm beyond bend 24, a width of about 1.0 mm, and a thickness of about 0.6 mm. Lower jaw 34 preferably has a length of about 15 mm beyond bend 30, a width of about 1.0 mm, and a thickness of about 0.6 mm. Upper handle 12 and lower handle 14 preferably have a length of about 8.4 cm and a width of about 1 cm. Forceps 10, including cannula 18, are preferably formed from stainless steel.

Figure 2:
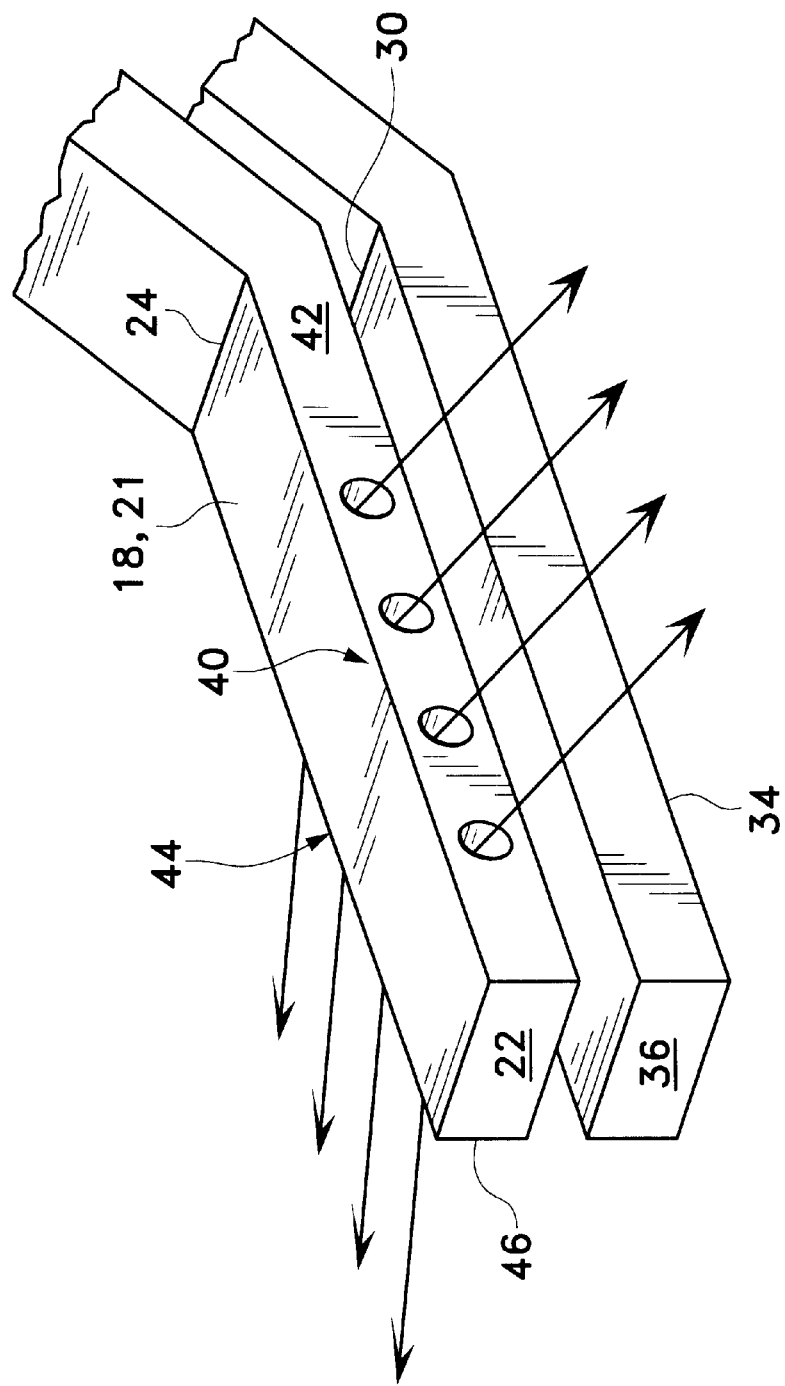
FIG. 2 is an enlarged, fragmentary view of the upper and lower jaws of the forceps of FIG. 1.

FIG. 2. illustrates an enlarged view of a preferred embodiment of upper jaw 21 (and thus the distal end of cannula 18) and lower jaw 34. As shown in FIG. 2, upper jaw 21 preferably has a generally rectangular cross-section. Upper jaw 21 has a plurality of spaced apertures 40 on a side 42 and a plurality of spaced apertures 44 (not visible in FIG. 2) on a side 46. Upper jaw 21 preferably has four apertures 40 having a diameter of about 0.2 mm and a spacing of about 1 mm to about 2 mm between each aperture. Apertures 44 preferably have an identical geometry and spacing to apertures 40.

Referring now to FIGS. 1–4, the preferred method of using forceps 10 to position an ICOL within an intracorneal pocket will now be described in greater detail. A human eye has a cornea having a diameter of about 12 mm. Therefore, the diameter of an ICOL 50 must be less than 12 mm, is preferably from about 5 mm to about 9 mm, and is most preferably about 7 mm. Intracorneal pocket 52 for receiving ICOL 50 preferably has a diameter about 1 mm larger than the diameter of ICOL 50. For the preferred diameter of ICOL 50 of 7 mm, intracorneal pocket 52 has a diameter of about 8 mm. Intracorneal pocket 52 is accessed via a conventional tunnel incision 54. Tunnel incision 54 preferably has a width of about 3 mm, a length of about 1.5 mm, and a depth of about 0.25 mm to about 0.3 mm from the outer surface of the cornea. A preferred method of forming intracorneal pocket 52, including tunnel incision 54, is described in more detail in U.S. application Ser. No. 09/434,912 mentioned hereinabove. For convenience of description, but not by way of limitation, the preferred method of using forceps 10 to position an ICOL within an intracorneal pocket will be described with reference to an intracorneal pocket 52 having a diameter of about 8 mm, a tunnel incision 54 having a width of about 3 mm, and an ICOL having a diameter of about 7 mm.

During the procedure, a surgeon first places ICOL 50 on a sterile surface in its proper orientation for insertion into the eye. The surgeon grasps ICOL 50 proximate its midline with upper jaw 21 and lower jaw 34 of forceps 10, insuring that the rounded, distal end 22 of upper jaw 21 and the rounded, distal end 36 of lower jaw 34 are proximate the far edge of ICOL 50.

The following steps are performed using an operating microscope to visualize the anterior aspect of the eye and after applying a topical anesthetic to the eye. Jaws 21 and 34, and ICOL 50, are positioned proximate the entrance of tunnel incision 54. The surgeon utilizes conventional forceps (not shown) to "prime" edges 56 and 58 of ICOL 50 to fold upwards while using forceps 10 to insert ICOL 50 into tunnel incision 54 in the direction of arrow 60. After passing through tunnel incision 54, ICOL 50 is then centered within intracorneal pocket 52.

The surgeon then activates reservoir 28 to provide surgical fluid to upper jaw 21 via cannula 18. Surgical fluid is ejected from apertures 40 and 44 of upper jaw 21 with enough force to spread, or to help spread, folded edges 56 and 58 of ICOL 50 into their proper flattened orientation, as indicated by dashed lines in FIG. 4. Apertures 40 and 44 are preferably formed so that a stream of fluid is ejected from each aperture for a distance of about 1 cm. The streams of surgical fluid ejected from apertures 40 and 44 are indicated by bolded arrows in FIGS. 2 and 4. Apertures 40 and 44 are preferably oriented so that the streams of surgical fluid are ejected at a downward angle of about 30 to about 45 degrees relative to the plane of upper jaw 21. The surgical fluid lubricates ICOL 50 and intracorneal pocket 52 during the unfolding of ICOL 50, minimizing any irritation of the stromal tissues. The surgical fluid also lubricates forceps 10, minimizing any irritation of the stromal tissues upon withdrawal of forceps 10.

After ejecting surgical fluid, the surgeon then makes a final positioning of ICOL 50 and withdraws forceps 10 from tunnel incision 54. Any excess surgical fluid drains out of intracorneal pocket 52 from tunnel incision 54 into the exterior of the cornea. A topical antibiotic/steroid is preferably placed in the eye after implantation of ICOL 50.

Using forceps 10, it has been observed that a surgeon may properly position ICOL 50 within intracorneal pocket 52 as described hereinabove in less than 30 seconds. In contrast, such positioning typically requires about 1.5 to 3 minutes using conventional intraocular lens folding forceps.

Figure 5:
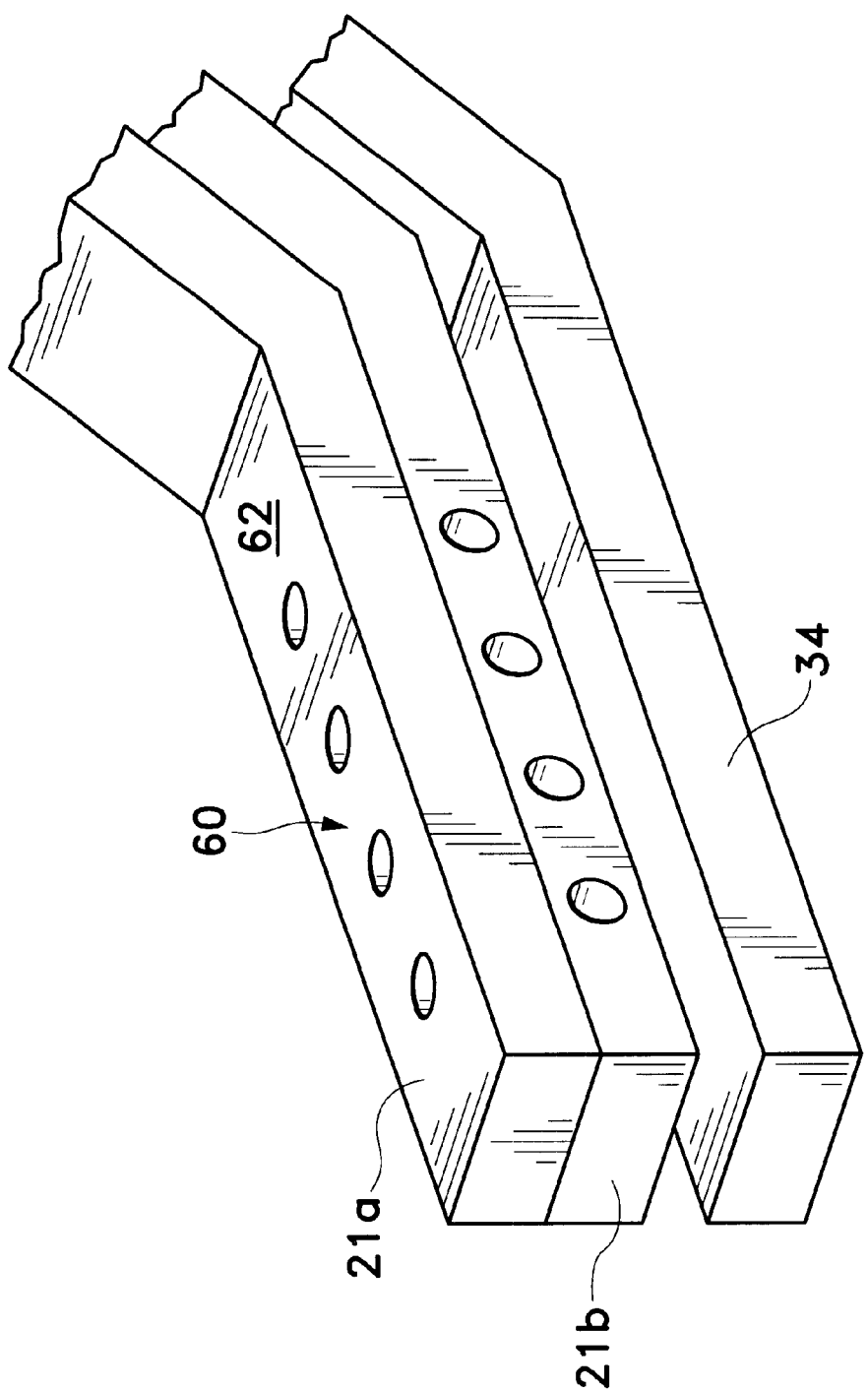
FIG. 5 is an enlarged, fragmentary view of a second preferred embodiment of the upper and lower jaws of the forceps of FIG. 1.

Referring now to FIG. 5, an enlarged view of a second preferred embodiment of the upper and lower jaws of forceps 10 is schematically illustrated. In this embodiment, forceps 10 has a first upper jaw portion 21a, a second upper jaw portion 21b disposed below upper jaw portion 21a, and a lower jaw 34. Upper jaw portion 21b preferably has an identical structure and operation as upper jaw 21 of FIGS. 1–4. Lower jaw 34 preferably has an identical structure and operation as lower jaw 34 of FIGS. 1–4. Upper jaw portion 21a has a structure similar to upper jaw 21 of FIGS. 1–4, except that upper jaw portion 21a has plurality of spaced apertures 60 on an upper surface 62 instead of a plurality of apertures 40 and 44 on its sides 42 and 46. Upper jaw portion 21 a preferably has four apertures 60 having a diameter of about 0.2 mm and a spacing of about 1 mm to about 2 mm between each aperture.

Referring to FIG. 1, upper jaw portion 21a is preferably a distal end of a second cannula (not shown) similar to cannula 18. This second cannula maybe disposed within, or coupled to a side 19, of upper handle 12. The proximal end of this second cannula extends from proximal end 25 of forceps 10 and terminates in a port 66. Port 66 is for fluidly coupling with a vacuum source 68. Such coupling is preferably performed using medical grade silastic tubing 67. Vacuum source 68 may comprise a syringe, a venturi coupled to a pneumatic pressure source, a pumping device, or another conventional source of vacuum.

Referring to FIGS. 1, 3, and 5, when "priming" edges 56 and 58 of ICOL 50 to fold upwards, the surgeon may activate vacuum source 68. Vacuum is supplied to apertures 60 of upper jaw 21a, insuring that edges 56 and 58 remain in a folded position. Upper jaw 21a thus facilitates the insertion of ICOL 50 through tunnel incision 54 and minimizes any irritation of stromal tissue. Once ICOL 50 is centered within intracorneal pocket 52, the surgeon deactivates vacuum source 68. The surgeon then activates reservoir 28 to eject surgical fluid to flatten ICOL 50, as described above. If the explanting of ICOL 50 is necessary at a later time, upper jaw 21a may also be used to insure that edges 56 and 58 remain in a folded position as ICOL passes through tunnel incision 54.

From the above, it may be appreciated that the present invention provides a microsurgical instrument that more effectively positions an ICOL within an intracorneal pocket. The instrument is easy for a surgeon to use, safe for the patient, and is relatively inexpensive.

The present invention is illustrated herein by example, and various modifications may be made by a person of ordinary skill in the art. For example, the geometries of the upper handle, lower handle, upper jaw, and lower jaw of the forceps may be different from that shown in the preferred embodiments. As another example, the length of the upper and lower jaws of the forceps may be changed to accommodate ICOLs and intracorneal pockets having various diameters. As a further example, apertures 60 may be located on the sides of upper jaw portion 21a. As a further example, apertures 60 may be located on lower jaw 34, and the cannula associated with apertures 60 may be disposed on or within proximal portion 32 of lower handle 14. As a further example, the forceps may be formed with only vacuum capability instead of only irrigating capability, or irrigating and vacuum capabilities, for certain applications of the present invention. As a further example, cannula 18 may be used to deliver a liquid pharmaceutical preparation. As a final example, the positions of upper jaw 21 and lower jaw 34, or upper jaw portions 21a and 21b and lower jaw 34, as shown in FIGS. 2 and 5 may be reversed in cases where the ICOL is "primed" by folding its sides downward instead of upward. In this case, apertures 42 and 44 are preferably oriented so that streams of surgical fluid are ejected at an upward angle relative to the plane of the jaws of the forceps. In addition, upper jaw portion 21b is preferably located above upper jaw portion 21a, and apertures 60 of upper jaw portion 21a are preferably located on its lower surface.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A microsurgical forceps for positioning an intracorneal optical lens within an intracorneal pocket, comprising:
   a first handle having a cannula for transporting surgical fluid and a first jaw with an aperture for delivering said fluid, wherein said cannula is for fluidly coupling to a reservoir of said fluid, wherein said first jaw is for receiving said lens in a folded position around said first jaw, and wherein said aperture ejects said fluid in an outward direction from said first jaw to help unfold said lens; and
   a second handle coupled to said first handle at a hinge point and having a second jaw for cooperating with said first jaw.

2. The forceps of claim 1 wherein:
   said first handle comprises a second cannula for fluidly coupling to a vacuum source; and
   said first jaw comprises a second aperture for providing vacuum.

3. The forceps of claim 1 wherein:
   said second handle comprises a second cannula for fluidly coupling to a vacuum source; and
   said second jaw comprises a second aperture for providing vacuum.

4. A microsurgical forceps for positioning an intracorneal optical lens within an intracorneal pocket, comprising:
   an upper handle having:
      a cannula for transporting surgical fluid, wherein said cannula is for fluidly coupling to a reservoir of said fluid; and
      an upper jaw with a first plurality of apertures for delivering said fluid, wherein said upper jaw is for receiving said lens in a folded position around said upper jaw, and wherein each of said first plurality of apertures ejects said fluid in an outward direction from said upper jaw to help unfold said lens; and
   a lower handle coupled to upper handle at a hinge point and having a lower jaw for cooperating with said upper jaw.

5. The forceps of claim 4 wherein:

said upper jaw comprises a first side and a second side;

said first plurality of apertures is disposed on said first side; and further comprising a second plurality of apertures disposed on said second side, wherein each of said second plurality of apertures ejects said fluid in an outward direction from said upper jaw to help unfold said lens.

6. The forceps of claim 4 wherein:

said upper handle comprises a second cannula for fluidly coupling to a vacuum source; and said upper jaw comprises a second plurality of apertures for providing vacuum.

7. The forceps of claim 4 wherein:

said lower handle comprises a second cannula for fluidly coupling to a vacuum source; and said lower jaw comprises a second plurality of apertures for providing vacuum.

8. A microsurgical forceps for positioning an intracorneal optical lens within an intracorneal pocket, comprising:

a first handle having a cannula for fluidly coupling with a vacuum source and a first jaw with at least one aperture for delivering said vacuum, wherein said first jaw is for receiving said lens in a folded position around said first jaw, and wherein said at least one aperture is for helping to hold said lens in said folded position; and a second handle coupled to said first handle at a hinge point and having a second jaw for cooperating with said first jaw.

9. A method of positioning an intracorneal optical lens within an intracorneal pocket, comprising the steps of:

providing a microsurgical forceps, comprising:

a first handle having a cannula for fluidly coupling to a reservoir of surgical fluid and a first jaw with an aperture for delivering said fluid; and a second handle coupled to said first handle at a hinge point and having a second jaw for cooperating with said first jaw;

grasping an intracorneal optical lens between said first jaw and said second jaw;

folding said lens around said first jaw;

inserting said lens into an intracorneal pocket in said folded position; and activating said reservoir to eject said surgical fluid from said aperture to help unfold said lens into a generally flattened position within said intracorneal pocket.

10. The method of claim 9 wherein:

said first jaw comprises a first aperture oriented in a first direction, and a second aperture oriented in a second direction opposite said first direction and for delivering said fluid; and said activating step comprises ejecting said fluid from said first and second apertures to help unfold said lens.

11. The method of claim 9 wherein:

said first handle comprises a second cannula for fluidly coupling to a vacuum source;

said first jaw comprises a second aperture for providing vacuum;

said folding step comprises activating said vacuum source so that said second aperture provides vacuum to help hold said lens in a folded position.

12. The method of claim 9 wherein:

said second handle comprises a second cannula for fluidly coupling to a vacuum source;

said second jaw comprises a second aperture for providing vacuum;

said folding step comprises activating said vacuum source so that said second aperture provides vacuum to help hold said lens in a folded position.

* * * * *